United States Patent [19]

Petree et al.

[11] 4,267,347
[45] May 12, 1981

[54] METHOD FOR DIRECT PREPARATION FOR 1,2,4-TRIAZOLE FROM HYDRAZINE AND FORMAMIDE

[75] Inventors: Harris E. Petree, Kernersville; Joseph R. Pociask, Greensboro, both of N.C.; John T. Gupton, Casselberry, Fla.

[73] Assignee: Ciba-Geigy Corporation, Ardsley, N.Y.

[21] Appl. No.: 92,257

[22] Filed: Nov. 7, 1979

[51] Int. Cl.³ .......................................... C07D 249/08
[52] U.S. Cl. .................................................... 548/262
[58] Field of Search ............................................ 548/262

[56] References Cited

FOREIGN PATENT DOCUMENTS 2802491 7/1979 Fed. Rep. of Germany ........... 548/262
61617 12/1970 Luxembourg ........................... 548/262

OTHER PUBLICATIONS

Kirk-Othmer, Encyclopedia of Chemical Technology, 2nd Edition, vol. 10, p. 104, (John Wiley, N.Y., 1966).

Primary Examiner—Alton D. Rollins
Attorney, Agent, or Firm—Karl F. Jorda

[57] ABSTRACT

Process for the preparation of 1,2,4-triazole comprises contacting hydrazine or its aqueous solutions with at least about 2.5 moles of formamide at a temperature of 140° to 210° C. and then recovering the resultant 1,2,4-triazole in yields of 92–98% with 94–98% purity. The formamide is maintained in an excess over about the 2.5 molar amount consumed in the reaction with the hydrazine. Recovery steps for isolating the 1,2,4-triazole are disclosed.

8 Claims, No Drawings

METHOD FOR DIRECT PREPARATION FOR 1,2,4-TRIAZOLE FROM HYDRAZINE AND FORMAMIDE

FIELD OF THE INVENTION

The present invention relates to a process for the direct preparation of 1,2,4-triazole from the controlled reaction of hydrazine with formamide and more particularly relates to the preparation and recovery of 1,2,4-triazole at high yields and in good purity.

BACKGROUND OF THE INVENTION 1,2,4-triazole is an important intermediate in the preparation of various agricultural and pharmaceutical products. Examples of such agricultural and pharmaceutical products are mentioned in U.S. Pat. Nos. 3,912,752 and 4,097,662.

A number of methods for making 1,2,4-triazole have been reported, including those mentioned in C. Ainsworth, *Org. Syn., Coll. Vol.* V, 1070 (1973) and the references cited therein. All of these prior art procedures suffer from low yields, require expensive reagents and equipment as well as multi-step reactions, or include reactions which are impractical by requiring conditions which are difficult to maintain for large scale production.

Anisworth (ibid.) also has reported a procedure which provides 1,2,4-triazole in an overall yield of 64% from hydrazine hydrate. This method involves making 1,2-diformylhydrazine in 80% yield from formamide and hydrazine hydrate and then heating the 1,2-diformylhydrazine at 200° C. in liquid ammonia under pressure (>1000 psi) for 24 hours to obtain, after distillation of the crude product, a 70-80% yield of the triazole based on diformylhydrazine.

OBJECTS OF THE INVENTION

It is an object of this invention to provide a method for the preparation of 1,2,4-triazole from relatively inexpensive raw materials at low pressures, preferably at atmospheric pressure, in a single step.

It is a further object of the invention to provide a single step method for the manufacture of 1,2,4-triazole without any external source of ammonia and with facile isolation and recovery of the product.

It is a further object of this invention to provide 1,2,4-triazole via a single step process in yields of 75 to 99% and of purity greater than 90%.

THE INVENTION

The process of the present invention provides for the preparation of 1,2,4-triazole by the steps of contacting and reacting, over an extended feed time, hydrazine or its aqueous solutions, with at least 2.5 and preferably 4 molar equivalents of formamide at a temperature of 140° to 210° C. and preferably 160° to 180° C. The reaction is run at atmospheric pressure. Ammonia, water, formic acid and ammonium formate, produced by the reaction are removed, and any excess formamide is then distilled from the reaction mixture leaving a residue of 1,2,4-triazole.

An equation for the reaction of the subject process is shown below:

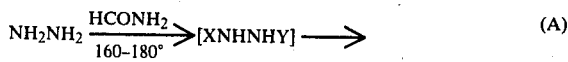

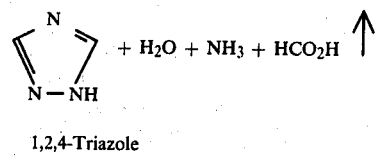

1,2,4-Triazole

The reaction intermediate XHNNHY might be monoformylhydrazine, diformylhydrazine or some other hydrazine-containing compound.

The mode of addition of hydrazine to hot formamide is crucial to the process of this invention. When this process is run under batch-wise conditions wherein the aqueous hydrazine and formamide are mixed at room temperature and then heated at e.g., about 170° C. for 1 to 7 hours, it has been demonstrated that the triazole yield is controlled by the amount of formamide reactant/solvent; larger formamide excesses provide higher yields and, concomitantly, lower levels of hydrazine-containing impurities. The relationship between the amount of formamide used and the triazole yield is clearly shown in Table 1 below:

TABLE 1

| HCONH$_2$/NH$_2$NH$_2$ | % Total Triazole Yield |
| --- | --- |
| 12.5 | 90.3 |
| 12.5 | 89.4 |
| 7.5 | 84.1 |
| 7.5 | 86.9 |
| 5.0 | 77.4 |
| 5.0 | 77.8 |
| 4.0 | 75.2 |
| 4.0 | 77.5 |

In batch reaction where lower formamide to hydrazine ratios gave lower yields, it was found that some of the hydrazine was converted to 4-amino-1,2,4-triazole. This side reaction is clearly due to hydrazine reacting with hydrazine-containing intermediates (B) or two equivalents of hydrazine-containing intermediates reacting together (C). Additionally, 4-N-formamidino-1,2,4-triazole is also formed by reaction of formamide with 4-amino-1,2,4-triazole (D).

Clearly, large formamide excesses (possibly up to 12.5 or even up to 20 or 30 molar equivalents) are necessary in the batch process in order to prevent hydrazine or hydrazine-containing intermediates from reacting with themselves to form 4-amino-1,2,4-triazole.

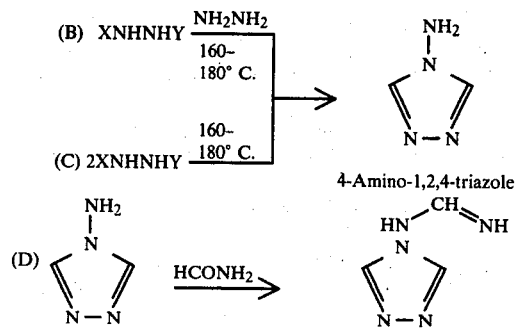

According to a preferred aspect mode of this invention, improved yields of high purity 1,2,4-triazole are obtained with low ratios of formamide to hydrazine when the reaction is carried out under conditions employing the slow addition of hydrazine to hot formamide. The preferred process entails the slow addition of aqueous hydrazine to formamide which has been preheated to about 170° C.±2° C. An addition time of 2-4 hours for the introduction of the hydrazine is advantageous. In addition, it is preferred to introduce the hydrazine below the surface of the liquid formamide as a fine stream. In such fashion, hydrazine-containing triazole precursors are kept at low concentrations in order to continually react directly with the formamide to form 1,2,4-triazole. Since the concentrations of hydrazine are miniscule at the time of the reaction, side reactions such as set forth in equations (B) through (D) above are minimized and the triazole yield is maximized.

It is preferred to use the hydrazine in the form of its hydrate (64% aqueous hydrazine). This material is liquid and is easily handled, but other concentrations of aqueous hydrazine can also be used. The reaction also proceeds with anhydrous hydrazine, but this entails difficulties in handling due to the lower stability of anhydrous hydrazine at the preferred reaction temperature, as well as due to its irritant and toxic properties.

In general, the reaction between formamide and hydrazine according to this aspect of this invention is quite simple. The aqueous hydrazine is added to four equivalents of formamide maintained at about 160° to 180° C., while the ammonia, water and formic acid are codistilled from the reaction vessel. The addition time is not critical, providing that the desired reaction temperature range is maintained while evolving large quantities of water and ammonia. The formic acid and the ammonia react to form ammonium formate which is also collected in the aqueous distillate. Hydrazine losses into the aqueous distillate are negligible at the stated temperature, while as shown in the non-limiting examples herein, unused formamide is recyclable.

The initial reaction between hydrazine and the hot formamide is very rapid. As the reaction proceeds quite rapidly, it is not essential that the reaction mixture be maintained at the reaction temperature for an extended length of time after the addition of the hydrazine is complete. The mixture, upon completion of the hydrazine addition, need not be held at the reaction temperature for longer than one and a half hours to ensure completeness of the reaction and to maximize the yield.

The preferred temperature range of 160° to 180° C. is based upon the observation that, at temperatures below about 160° C., the reaction rate falls off rapidly and the formation of 1,2,4-triazole proceeds slowly. At temperatures above about 180° C., the formamide decomposition rates become significant.

The 1,2,4-triazole obtained according to the present invention is isolated from the reaction mixture by several expedients. It is possible to crystallize the 1,2,4-triazole from the excess formamide in reaction mixtures after water has been distilled out. Formamide retained on the triazole precipitate can be washed out using a suitable organic solvent (e.g., methyl ethyl ketone, tetrahydrofuran, ethyl acetate). Only 40-50% of the available triazole can be recovered by this method, necessitating recycle of the triazole-containing filtrate.

In order to isolate the triazole it is preferred to remove the excess formamide by vacuum distillation at reduced pressure of e.g., 20-100 mm of Hg. Under conditions of a distillative workup in batch mode the first third of the distillate, which has a boiling point range of 95°-110° C. at 20-30 mm Hg, contains only about 30% of formamide. This cut can be retained for redistillation. The remainder, boiling in the range of 110°-135° C. at this pressure range, contains about 85% formamide. It is suitable for direct recycling into the next succeeding reaction batch. In addition to about 1% of the 1,2,4-triazole, the impurities present in the formamide distillate are primarily water, formic acid and ammonium formate.

Assuming that about 2.5 equivalents of formamide are consumed in the triazole formation, the recovery of the formamide excess in the second distillation cut ranges from 75 to 90% of the excess of formamide originally charged. In addition, about 70% of the formamide present in the first cut can be salvaged by redistillation. This vacuum distillation is an economical expedient in the overall preparation of the 1,2,4-triazole according to this invention. The formamide, obtained in the second distillation cut, about 85% purity, can be directly recycled into the reaction without any apparent harm to triazole formation in succeeding batches.

After the formamide is removed by the vacuum distillation procedure set forth above, the triazole can be recovered by one of two methods: (1) the residual melt can be directly cast on a cooled surface and reduced into thin particle fragments, or (2) a suitable solvent can be added to 1,2,4-triazole and the triazole then recrystallized from this solvent. Recrystallization, of course, provides a purer product.

The recovery of 1,2,4-triazole directly from the melt in a distillation vessel is a simple isolation technique. No yield losses are incurred and no additional material are added to the product. The triazole directly isolated from the melt is usually 94% pure and contains 0.5 to 1.2% of 4-N-formamidino-1,2,4-triazole and from 0.3 to 0.4% of 4-amino-1,2,4-triazole. Other impurities including water, formic acid and formamide, are present in total quantities of less than 0.6%. Recovery of the triazole as a melt does not cause appreciable decomposition of the triazole. Although the 1,2,4-triazole obtained from the melt is about 94% pure, the color of the molten material varies from light mustard tan to dark brown or reddish brown. If material having less color is desirable, the formamide can be distilled from the reaction mixture at lower distillation pressures so that the pot temperature is lower and less colored materials are formed.

It has also been found that continuous distillation will reduce discoloration. Under the conditions of continuous distillation, residual decomposition products can be minimized, thus yielding lighter colored products. However, the about 94% purity material is adequate for the synthesis of agricultural fungicides, antimicrobials and other pesticide products, which are the major uses of the 1,2,4-triazole.

The 1,2,4-triazole can also be obtained in purer form (98+% purity) by recrystallizing the 1,2,4-triazole melt from a suitable solvent. Non-limiting examples of satisfactory solvents include ethyl acetate, tetrahydrofuran, methyl ethyl ketone and formamide. Equivalent solvents are of course suitable.

Recrystallation provides a purer product than the product from the direct melt recovery. This purer product assays in the range of 96-98+% 1,2,4-triazole and contains less than 0.3% of 4-N-formamidino-1,2,4-triazole and less than 0.1% of 4-amino-1,2,4-triazole.

When recrystallization recovery is completed using ethyl acetate, the average isolated yield is 87% and an additional 9% of 1,2,4-triazole is contained in the mother liquor. About 70% of the product in the mother liquor can be recovered by distilling off the solvent and then slurrying the residue in tetrahydrofuran or methyl ethyl ketone. Thus, total yields approaching 93% can be realized after reworking the recrystallization mother liquors.

It should be noted that all of the steps of this invention may be carried out in a continuous mode when chemical operations equipment are selected by persons knowledgeable in the art.

EXAMPLE 1

A three liter, five-neck, round bottom flask is charged with 1,440 g formamide (32 moles). The temperature of the formamide is then raised to 170° C. and maintained in the range of 170°-172° by the use of a temperature controller. Hydrazine hydrate (64% hydrazine; 400.5 g; 8.0 moles) is then slowly introduced as a fine stream under the surface of the stirred formamide at a rate of about 2-3 moles per hour. During the hydrazine addition, a vigorous evolution of ammonia, water and formic acid takes place which is distilled out of the reaction vessel through a suitable distillation column. It is advantageous to maintain the vapor temperature in the overhead of the column at less than 100° C. in order to minimize losses of formamide. After the addition of the hydrazine is completed, the temperature of the reaction mix is maintained at the 170° C. temperature for 1½ hours. The reaction mixture is then cooled to ambient temperature and provides a light yellow solution which crystallizes on standing. The yield is 1,200-1,250 g of this solution containing 42-45% 1,2,4-triazole corresponding to an in situ yield of 95-98%. The isolation of 1,2,4-triazole will be described in the following examples.

EXAMPLE 2

The flask containing the reaction mixture obtained in Example 1, after holding at 170° C. for 1½ hours, is attached to a vacuum distillation apparatus and the system is brought to an equilibrium at 20 mm Hg. Heating is begun and an initial cut is made, collecting 150-175 ml of distillate. The overhead temperature at this point is in the range 105°-110° C. This cut contains approximately 30% formamide. The distillation is continued at an overhead temperature in the range 115°-120° C. until 350-400 ml of distillate is collected. Heating is now discontinued to prevent the temperature of the residue from exceeding 130° C. The yield is 540-570 g of a reddish brown melt containing 93-95% 1,2,4-triazole for a total yield of 92-97% (based on hydrazine). The 1,2,4-triazole is cooled and reduced to thin flakes, which may be further cominuted if desired.

EXAMPLE 3

The melt obtained in Example 2 may be cooled in the vessel to about 80° C. and sufficient solvents such as methyl ethyl ketone, tetrahydrofuran, ethyl acetate, formamide, etc., are added to the 1,2,4-triazole in the vessel. The flask contents are then stirred and heated until the 1,2,4-triazole completely dissolves. The solution is then cooled to 10° C. and the resulting slurry is filtered and the crystalline 1,2,4-triazole is dried. Yield: 480-510 g of light brown to light red crystals containing 96-98% of 1,2,4-triazole for a yield of 84-90%. The mother liquor is then concentrated by distillation in suitable equipment, enabling solvent recovery. The residual product thus recovered and washed with tetrahydrofuran or methyl ethyl ketone may be used as is, or further purified, with an overall yield of 92 to 94%.

As various possible modifications of the described embodiments of this invention may be made (such as continuous mode of operation of all herein described operational steps), it is to be understood that all art-recognized equivalents of the matter herein described are to be included and that the examples and descriptions are to be interpreted as illustrative and not in a limiting sense.

What we claim is:

1. The process for the preparation of 1,2,4-triazole which comprises the steps of introducing, below the surface of liquid formamide maintained at a temperature of 160° to 180° C., a stream of hydrazine or its hydrate, said formamide being present in a molar ratio of at least 4:1 to the introduced hydrazine; removing the gaseous $NH_3$, $H_2O$ and HCOOH and the reaction products thereof from the reaction mixture; distilling the excess unreacted formamide and then recovering the residual 1,2,4-triazole.

2. The process for the preparation of 1,2,4-triazole according to claim 1 wherein said hydrazine is used as an aqueous solution.

3. The process according to claim 1 wherein the unreacted formamide is distilled from the reaction mix at pressures below about 100 mm Hg.

4. The process according to claim 1 wherein the recovery of said 1,2,4-triazole, after the vacuum distillation of the formamide, is via a melt at a temperature above 120°, its melting point, followed by cooling to the solid state.

5. The process according to claim 1 wherein the recovery of said 1,2,4-triazole is by recrystallization from a solvent selected from the group consisting of ethyl acetate, tetrahydrofuran, methyl ethyl ketone and formamide.

6. The process according to claim 5 wherein said solvent for recrystallization is methyl ethyl ketone or ethyl acetate.

7. The process according to claim 1 wherein water is removed from the finished reaction mixture, the triazole crystallized from the residual formamide, the solid removed by filtration and washed with a suitable organic solvent to remove the formamide.

8. The process according to claim 1 wherein all operational steps are performed continuously.

* * * * *